(12) United States Patent
Shen et al.

(10) Patent No.: US 6,643,012 B2
(45) Date of Patent: Nov. 4, 2003

(54) APERTURELESS NEAR-FIELD SCANNING RAMAN MICROSCOPY USING REFLECTION SCATTERING GEOMETRY

(75) Inventors: Ze Xiang Shen, Singapore (SG); Wanxin Sun, Singapore (SG)

(73) Assignee: National University of Singapore (SG)

( * ) Notice: Subject to any disclaimer, the term of this patent is extended or adjusted under 35 U.S.C. 154(b) by 0 days.

(21) Appl. No.: 10/078,711

(22) Filed: Feb. 21, 2002

(65) Prior Publication Data

US 2002/0154301 A1 Oct. 24, 2002

Related U.S. Application Data

(60) Provisional application No. 60/270,830, filed on Feb. 23, 2001.

(51) Int. Cl.$^7$ ............................. G01J 3/44; G01N 21/65
(52) U.S. Cl. ....................................... 356/301
(58) Field of Search ........................ 356/301

(56) References Cited

U.S. PATENT DOCUMENTS

| | | | |
|---|---|---|---|
| 5,017,007 A | | 5/1991 | Milne et al. |
| 5,479,024 A | | 12/1995 | Hillner et al. |
| 5,864,397 A | | 1/1999 | Vo-Dinh |
| 6,002,471 A | * | 12/1999 | Quake ........................ 356/301 |

OTHER PUBLICATIONS

S. Webster et al., "Raman Microscopy Using A Scanning Near–Field Optical Probe", Vibrat. Spectrosc. vol. 18 (1998), pp. 51–59.

E.J. Ayars et al., "Surface Enhancements In Near–Field Raman Spectroscopy", Appl. Phys. Lett. vol. 76, No. 26, (2000), pp. 3911–3913.

R.M. Stockle et al., "Nanoscale Chemical Analysis By Tip–Enhanced Raman Spectroscopy", Chem. Phys. Lett., vol. 318, (2000), pp. 131–136.

C.L. Jahncke et al., "Raman Imaging With Near–Field Scanning Optical Microscopy", Appl. Phys. Lett., vol. 67, (1995), pp. 2483–2485.

M.N. Islam et al., "High–Efficiency And High–Resolution Fiber–Optic Probes For Near Field Imaging And Spectroscopy", Appl. Phys. Lett. vol. 71, (1997) pp. 2886–2888.

T. Yatsui et al., "Increasing Throughput Of A Near–Field Optical Fiber Probe Over 1000 Times By The Use of A Triple–Tapered Structure", Phys. Lett. vol. 73, (1998), pp. 2090–2092.

O. Martin et al., "Generalized Field Propagator For Electromagnetic Scattering And Light Confinement", Phys. Rev. Lett., vol. 74, No. 4, (1995), pp. 526–529.

Y.H. Chuang et al., "A Simple Chemical Etching Technique For Reproducible Fabrication Of Robust Scanning Near–Field Fiber Probes", Rev. Sci. Instrum., vol. 69, No. 2, (1998), pp. 437–439.

* cited by examiner

*Primary Examiner*—F. L. Evans
(74) *Attorney, Agent, or Firm*—Birch, Stewart, Kolasch & Birch, LLP

(57) ABSTRACT

An apertureless near-field scanning Raman microscope using reflection geometry. A laser beam focused to a small spot size on a sample onto which a silver coated metal probe is positioned. With this arrangement, it is possible to obtain enhanced near-field spectroscopy using reflection geometry. Near-field spectroscopic mapping can be done in a short time without extensive sample preparation.

18 Claims, 7 Drawing Sheets

APERTURELESS NEAR-FIELD SCANNING RAMAN MICROSCOPY USING REFLECTION SCATTERING GEOMETRY

CROSS-REFERENCE TO RELATED APPLICATION

This application claims benefit of U.S. Provisional Application No. 60/270,830, filed Feb. 23, 2001.

BACKGROUND OF THE INVENTION

1. Field of the Invention

The present invention relates generally to a near-field scanning Raman spectroscope and more particularly to apertureless near-field scanning Raman spectroscopy of the reflection type.

2. Description of Related Art

Raman spectroscopy is a technique that has been used for many years to measure molecular vibrations, which can then be used to determine the structure and chemical bonding of a sample. Light which shines on a sample experiences a wavelength shift due to the vibration of the molecules. Information can be determined from the spectrum of wavelengths that occur as to the make-up of the sample and to determine the chemical bonding and information of the constituent atoms. While this well-known system has been utilized to great advantage for decades, it has a spatial resolution in the micron range. It is desirable to extend the range in which this measurement can be used for purposes of examining nano-devices, quantum dots and single molecules of biological samples.

Recently, Raman spectroscopy has been combined with near-field scanning optical microscopy to form a technique known as near-field scanning Raman microscopy (NSRM). This is based on the principle used in near-field scanning optical microscopy (NSOM) of using an optical fiber having a small aperture to deliver laser light and keeping the fiber at a close constant distance (on the order of tens of nanometers) above the sample surface. By using such an optical fiber, it is possible to limit the laser spot size and scan the fiber tip across the sample surface. The resultant Raman signal is collected using a microscopic objective or a lens. The collected light is coupled to a Raman spectrometer where the Raman spectra are recorded for each point on the sample. An NSRM image is constructed using the spectra.

This type of device has been described in a series of published articles including S. Webster, D. A. Smith and D. N. Batchelder, *Raman microscopy using a scanning near-field optical probe*, Vibrat. Spectrosc. 18 (1998) 51, E. J. Ayars and H. D. Hallen, *Surface enhancement in near-field Raman spectroscopy*, Appl. Phys. Lett. 76 (2000) 3911, C. L. Jahncke, M. A. Paesler and H. D. Hallen, *Raman imaging with Near-field scanning optical microscopy*, Appl. Phys. Lett. 67 (1995) 2483, M. N. Islam, X. K. Zhao, A. A. Said, S. S. Mickel and C. F. Vail, *High-efficiency and high-resolution fiber-optic probes for near-field imaging and spectroscopy*, Appl. Phys. Lett. 71 (1997) 2886, T. Yatsui, M. Kourogi and M. Ohtsu, Appl. *Increasing throughput of a near-field optical fiber probe over 1000 times by the use of a triple-tapered structure*, Phys. Lett. 73 (1998) 2090, and Y. H. Chuang, K. G. Sun, C. J. Wang, J. Y. Huang and C. L. Pan, *A simple chemical etching technique for reproducible fabrication of robust scanning near-field fiber probes*, Rev. Sci. Instrum. 69 (1998) 437.

Because this type of system provides the incoming laser light through a very small aperture in the optical fiber, the light is extremely weak. Despite extensive efforts to fabricate fiber tips with a higher throughput, the strength of the light is still quite low. In addition, the Raman signal is intrinsically weak (typically less than 1 in $10^7$ photons). A typical Raman spectrum takes several minutes to collect using this type of near-field technique, making it prohibitive to construct a Raman image this way. For example, Raman images reported in some of the references cited above, took more than 9 hours to collect data.

An alternative approach to the fiber tip is the use of an apertureless metal tip. A system of this type has been discussed in R. M. Stöckle, Y. D. Suh, V. Deckert and R. Zenobi, *Nanoscale chemical analysis by tip-enhanced Raman spectroscopy*, Chem. Phys. Lett 318 (2000) 131. In this system, the light is not provided from the fiber tip, but instead a metal tip is placed within a focused light beam in order to enhance the Raman signal by several orders of magnitude. It is believed that this enhancement is a result of local field enhancement by the metal tip which is either due to the enhancement of the electromagnetic field in the vicinity of sharply pointed metal needle, or due to the excitation of surface plasma by the laser electromagnetic wave, or increased polarizability of the sample due to the interaction between the tip and the sample. This type of system has been used to record Raman images using a transmission mode. That is, the sample must be either transparent or very thin so that the light can travel therethrough. While this type of technique is a major step forward, it has the drawback that many samples are not transparent, and that it is often desirable not to take thin samples. Accordingly, this type of technique is not suitable for a reflection type geometry which is desirable in many cases.

SUMMARY OF THE INVENTION

Accordingly, one object of the present invention is to provide an apertureless near-field scanning Raman microscopy system.

Another object of the present invention is to provide a novel near-field scanning Raman microscopy system using reflection geometry.

A still further object of the present invention is to provide an apertureless near-field scanning Raman microscopy system using reflection geometry.

A still further object of the present invention is to provide a nano-scopic Raman imaging technique using near-field enhancement.

Another object of the present invention is to provide an apertureless near-field scanning Raman microscopy system using a bent metal tip to enhance the near-field signal.

Briefly these and other objects of the present invention are achieved by providing a laser beam focused by a microscopic objective to a small spot on a sample with a bent metal tip touching (contacting with or close to) the surface within the spot of light. The presence of the metal tip enhances the near-field signal so that the quality of the Raman spectrum is improved and so that that time necessary to collect the spectrum is much smaller.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
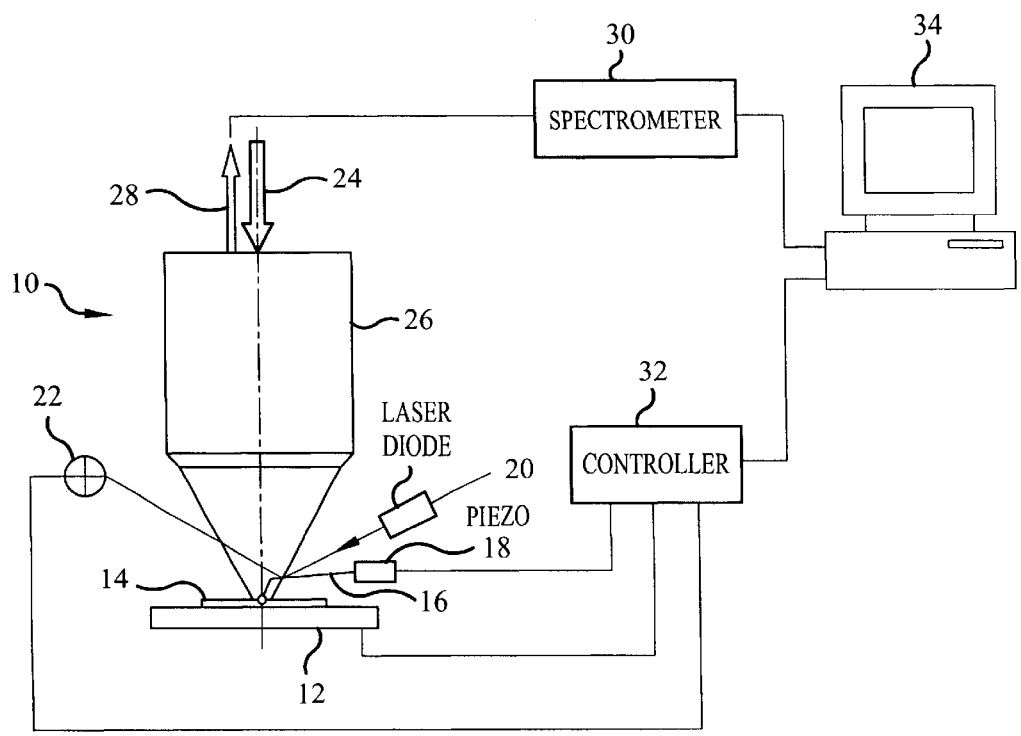
FIG. 1 is a schematic diagram of a first embodiment of the present invention.

Referring now to the drawings wherein like reference numerals designate identical corresponding parts throughout the several views, and more particularly to FIG. 1 thereof, wherein a first embodiment 10 of the present invention is shown. In this system, a scanning stage 12 is provided onto which a sample 14 is placed. A metal tip 16 is placed very near the sample and extends upwardly at an angle from the sample. The tip then is cantilevered almost horizontally and its far end is connected to a driving piezo device 18 which causes the metal tip to vibrate up and down when driving voltage is applied. A small laser diode 20 projects a beam onto the tip which is reflected and received by a quadrant detector 22 which can measure the vibrational amplitude or the bending degree of the cantilever. The piezo driver, the stage and the quadrant detector are all connected to a controller 32, which drives the X-Y (along horizontal plane) scan of the sample and move the sample up and down in accordance with information provided by the quadrant detector. Laser diode 20 is only used for this positioning information and is not the main laser provided for the spectrographic analysis.

The main laser light 24 is provided from above and is directed to the sharp tip end. The laser providing this beam is not shown in the Figure. The beam is focused using a microscope objective 26 so that a small spot is obtained around the tip end on the sample. The scattered light is collimated through the microscope objective 26 to form the Raman signal light 28. This is analyzed in the Raman spectrometer 30 and the results sent to the computer 34 for storage and analysis. The computer is also connected to the controller so as to receive information regarding the location of the sample.

Figure 2:
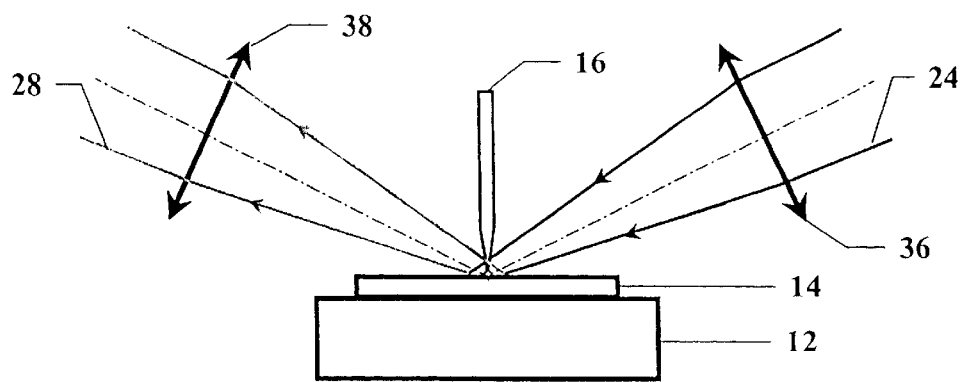
FIG. 2 is a schematic diagram of a second embodiment of the present invention.

A second embodiment is shown in FIG. 2 where the light is focused from the side and the tip is vertical. As shown in FIG. 2, stage 12 continues to hold sample 14 but tip 16 extends in a vertical direction from the sample. The light beam 24 is focused by lens 36 to a small spot around the tip end on the sample. The reflected light 28 carrying the Raman information is reflected to the other side where it is focused by lens 38. The condensed light is then sent to a spectrometer 30 in the same manner as in FIG. 1. In this arrangement, the metal tip can be brought to the sample surface by a tuning fork or cantilever and the Raman signal light can be collected using lens 36 instead, or by using both lens 36 and 38.

Figure 3:
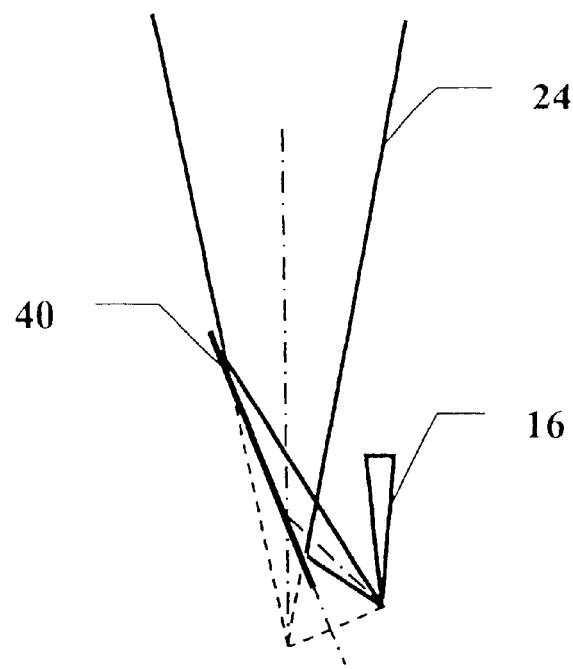
FIG. 3 is a diagram showing the mounting of a mirror used in the second embodiment of the present invention.

FIG. 3 shows a modification of the embodiment of FIG. 2 to simplify the apparatus. In this Figure tip 16 remains vertical, but it is desirable to avoid using an oblique objective, which requires a specially designed microscope and an objective with a longer distance. Instead, a mirror 40 is attached to the mount for the tip so that the converging laser beam 24 is reflected onto the tip from the side. In this arrangement, the bottom edge of the mirror is very close to the tip, perhaps less than 1mm.

Thus, as seen in each of FIGS. 1–3, the analysis of the Raman shifted light is based on a reflection geometry. This arrangement has a great advantage over aperture type reflection systems because the incoming light is much more powerful because it does not have to be carried through a very small aperture. As a result, the strength of the reflected light is considerably stronger. This arrangement also allows reflection type geometry rather than transmission type geometry in an apertureless system. This is largely due to enhancement of the signal from locations near to the tip end as opposed to locations which are farther away. That is, it is not possible to focus the light to a point as small as the size of the tip end. In order to receive clear signals, it is necessary that the near-field signal be comparable with or stronger than the far-field signal. In order to do this, it is necessary that the near-field signal be enhanced so that it can be easily and quickly detected. The near-field enhancement factor using the present arrangement is estimated to be at least $10^4$ times the un-enhanced signal. This is due to one or more of the following factors:

Enhancement of the electric field at the metal tip due to the nature of a sharp tip or excitation of surface plasma in the presence of an electromagnetic wave;

Proximity of a metal tip with the target sample within a very small distance increases the polarizability of the sample;

The incident angle of the laser;

The polarization of the laser source;

The power of the laser source;

The bending of the metal tip to allow the lasers to reach the tip without obstruction;

The ability to focus the light to form a small diameter spot; and

The coating of the metal tip with material which enhances the near-field when used with certain wavelengths.

While many different arrangements of specific instruments is possible, one example that has been utilized includes a standard Nanonics NSOM system and a Renishaw Raman spectrometer. Nanonics NSOM system uses a bent tip (cantilevered tip), which makes the scanning head very compact. The compact design allows the easy integration of the spectrometer and NSOM by putting the scanning head under the microscope objective (Nikon, x50, WD 13.8 mm and NA 0.45) of the Renishaw system, as shown in FIG. 1. An argon ion laser (488 nm line) is focused onto the metal tip, which is made from tungsten wire through electrochemical etching (similar to the method used in STM tip preparation) and then coated with silver through RF-sputtering. The interaction between the tip and the laser enhances the local electrical field near the tip, which in turn enhances the Raman signal nearby. The same objective lens collects the Raman signal from the laser spot in the back-scattering geometry, which includes both the far-field and near-field Raman signal, which are coupled into the spectrometer by coupling optics. The Renishaw spectrometer is driven by Dynamic Data Exchange technique, which allows third party software to control it. The NSOM system is controlled by a Burleigh controller and the software controls the Renishaw spectrometer as well, while running an AFM scan. During a scan, the tip is fixed relative to the laser spot while the sample runs a raster scan. After the scan, the Raman spectra obtained point by point are processed by an Array Basic program developed by ourselves. In this configuration, the tip apex is not shadowed as the laser beam is a focused beam with a converging angle of 26.7°, while the half angle of the tip is only about 4°. In addition, the tip is not perpendicular to the sample surface.

Figure 4:
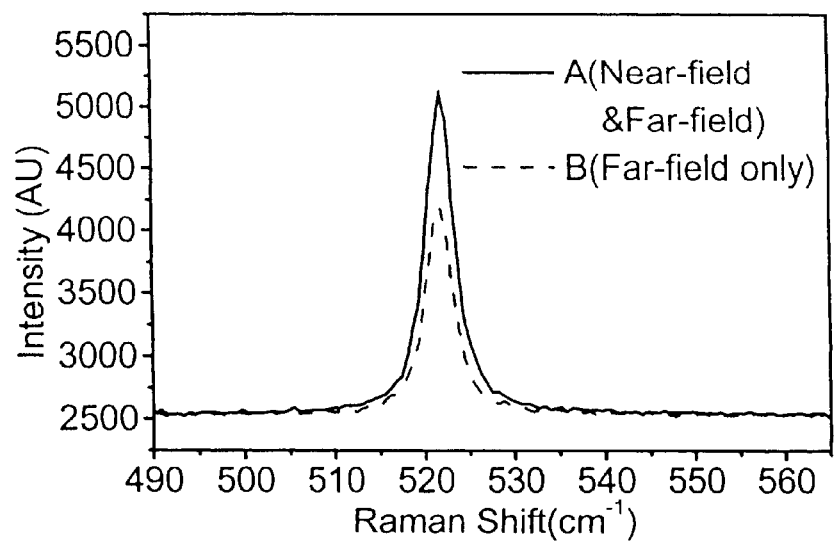
FIG. 4 is a graph showing the intensity of the measured Raman signal under two conditions.

Using this arrangement, a first experiment was performed on a pure Si single crystal to show near-field enhancement of the NSRM. A blank silicon wafer was placed on the scanning stage of the system and the silicon Raman peak at 520 cm$^{-1}$ was recorded by the Raman spectrometer for two tip positions. The first position has the tip touching (i.e., contacting with or close to) the silicon surface to record the Raman spectrum including both the near-field and the far-field components. The second position is with the tip lifted from the surface to record only the far-field Raman spectrum. FIG. 4 is a graph which shows the results of this experiment. The solid line indicates the situation where a tip touches (contacts with or is close to) the sample while the dotted line indicates the situation where the tip is lifted. It can be seen that about 35% of the total signal in the first situation is due to the near-field component. It is possible to estimate the enhancement factor, since the laser spot size is about 3 $\mu$m and the penetration depth of the 488 nm laser into the Si sample is about 0.5 $\mu$m. If the diameter of the metal tip is 100 nm, and the near-field enhancement occurs at a depth of 20 nm of Si sample, the enhancement is larger than $10^4$. This far-field signal comes from a volume of $\pi(3000/2)^2 \times 500$ nm$^3$ while the near-field signal comes from a much smaller volume of $\pi(100/2)^2 \times 20$ nm$^3$. The enhancement factor can then be estimated as $$\frac{I_n}{I_f} \times \frac{V_f}{V_n} = 12,115$$

where $I_n$=0.35 I and $I_f$=(1−0.35) I are measured near and far-field Raman intensity, respectively.

In addition to this calculation, it possible to compute the electrical field on the sample plane using a field propagator method taught by Olivier J. F. Martin, Christian Girard and Alain Dereux, *Generalized field propagator for electromagnetic scattering and light confinement*, Phys. Rev. Lett. 74 (1995) 526. This method starts from Maxwell's equation and obtains the electrical field as follows:

$$E(\bar{r}) = \int d\bar{r}' [\delta(\bar{r}-\bar{r}') - k^2 G(\bar{r},\bar{r}',\omega) \cdot \epsilon_s(\bar{r}',\omega)] \cdot E^0(\bar{r}'),$$

where k is the wave number in vacuum (k=|k̄|). $G(\bar{r},\bar{r}',\omega)$ is the Green's tensor associated with the whole (scattering and background) system. $E^0(\bar{r}')$ is the incident electrical field and $\epsilon_s(\bar{r}')$ is dielectric contrast of the scattering object (metal tip in this case) to the background.

The main task is to obtain the Green's tensor, which can be expressed analytically for a homogeneous background ($G^0(\bar{r},\bar{r}',\omega)$). The Green's tensor associated with the whole system can be obtained through Dyson's equation:

$$G_{i,j} = G^0_{i,j} - k^2 \sum_{p=1}^{N} G^0_{i,p} \epsilon^s_p G_{p,j} \Delta_p.$$

This is the discretized Dyson's equation, where $\Delta_p$ is the volume of $p^{th}$ mesh, N is the total number of meshes.

Figure 7:
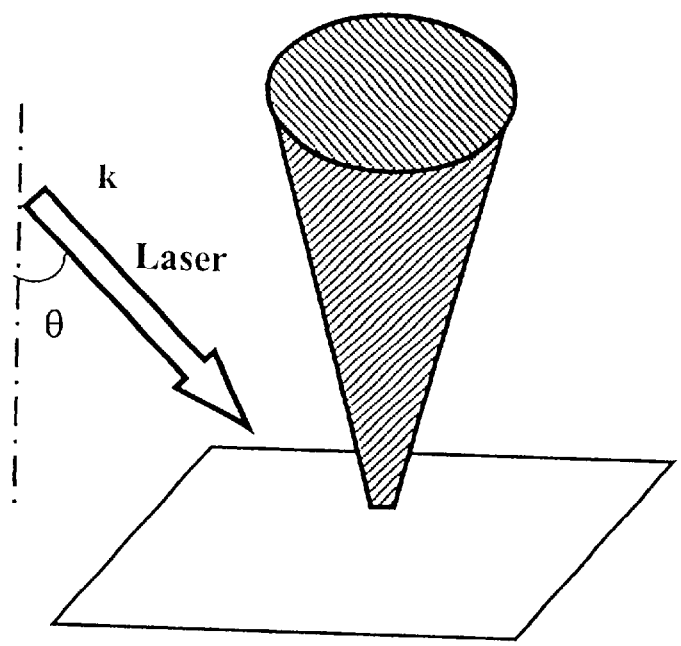
FIG. 7 is a diagram showing the parameters used in a simulation.

The incident beam used in the simulation is a parallel beam with a wavelength of 488 nm and intensity of 1. The tip is a conical silver tip, with a half angle of 15° and the size of tip apex $\lambda/80$ (around 6 nm for 488 nm laser), as shown in FIG. 7. In the simulation, the influence of sample on the electrical field is neglected.

Figure 8A:
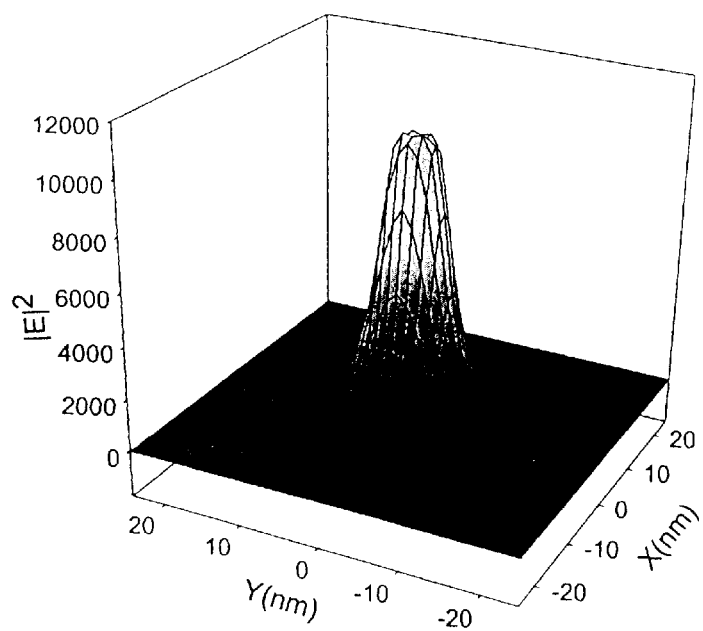
FIGS. 8A and 8B show the results of the simulation.
Figure 8B:
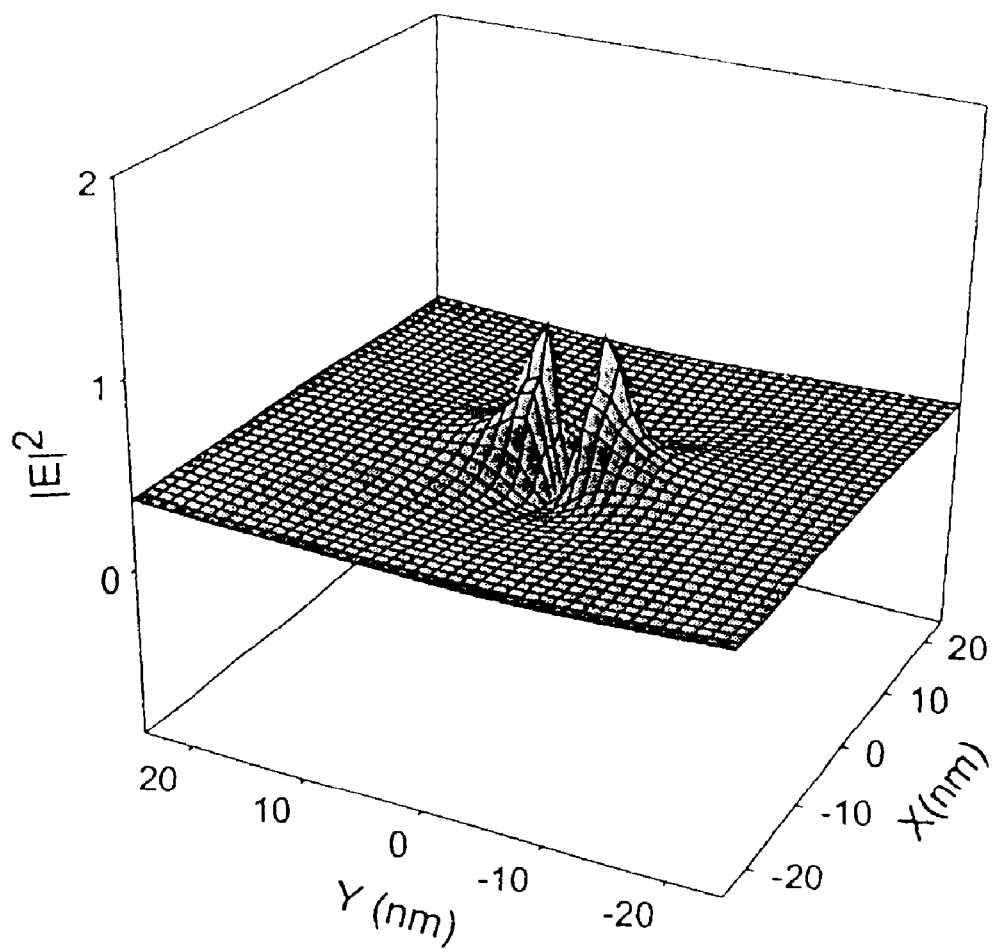
Figure 9:
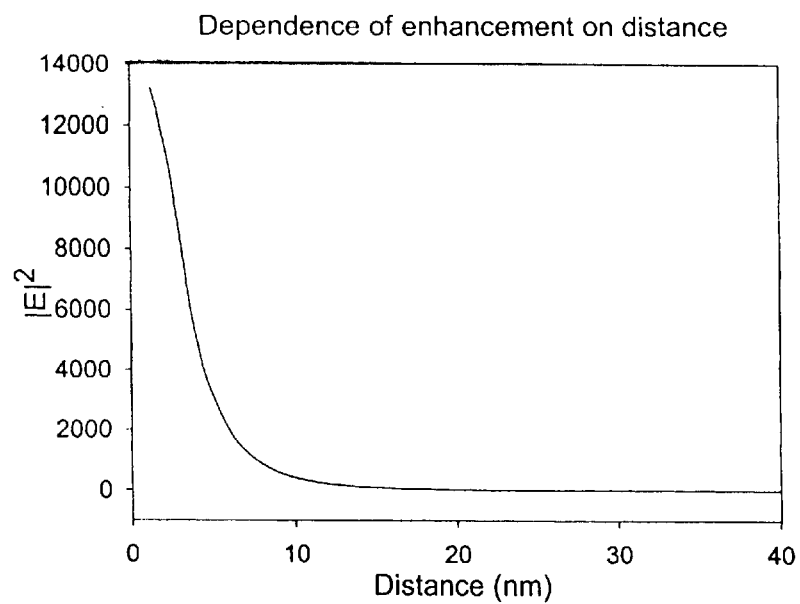
FIG. 9 is a graph showing the relationship between the enhancement factor and the distance.

FIGS. 8a and 8b show the simulation results with p-polarized and s-polarized incident beams respectively. Obviously, the near-field enhancement factor for p-polarized incident beam is much greater than the that for s-polarized incident beam. Therefore, p-polarization is preferred for near-field enhancement. If we take the full width at half maximum (FWHM) of the peak in FIG. 8a as the spatial resolution of the apertureless NSOM, the spatial resolution is about one and a half of the tip size, as shown in FIG. 8a. To simulate the spatial resolution in z-direction, we calculated the near-field enhancement factor under different distance between the observation plane and tip end. As shown in FIG. 9, the enhancement factor decays rapidly with the increase of the distance. So near-field signal comes from a very thin layer of the sample.

Figure 10:
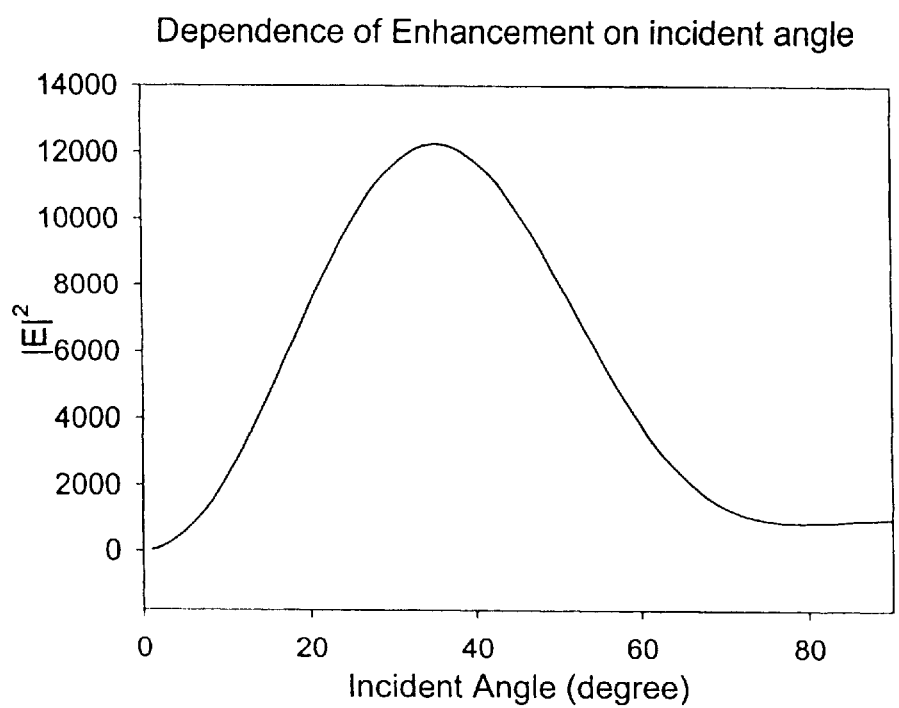
FIG. 10 is a graph showing the relationship between the enhancement factor and the incident angle.

Besides polarization, we have also simulated the effect of incident angle on the enhancement factor, shown in FIG. 10. From the previous results, the electrical component along the tip axis plays an important role in near-field enhancement. One would expect maximum enhancement when the incident angle tends to $\pi/2$. But the maximum enhancement does not occur at $\pi/2$. The incident angle at which the enhancement reaches maximum changes with the tip geometry.

Figure 5A:
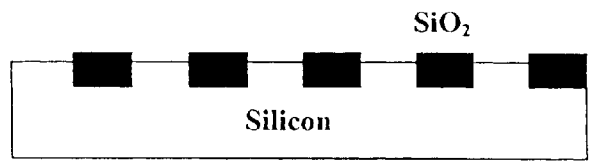
FIGS. 5A and 5B show the sample used in the second experiment, using the present invention.
Figure 5B:
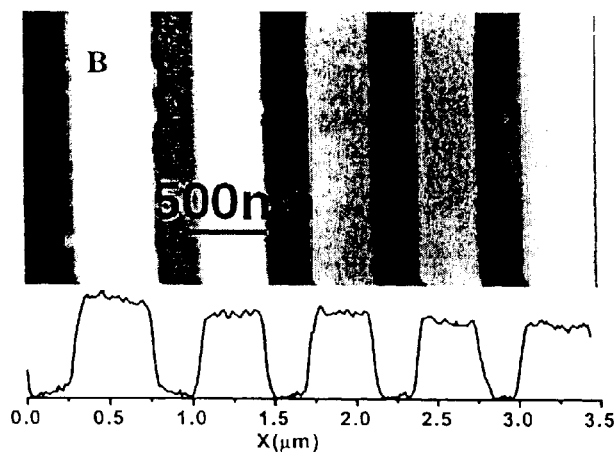
Figure 6:
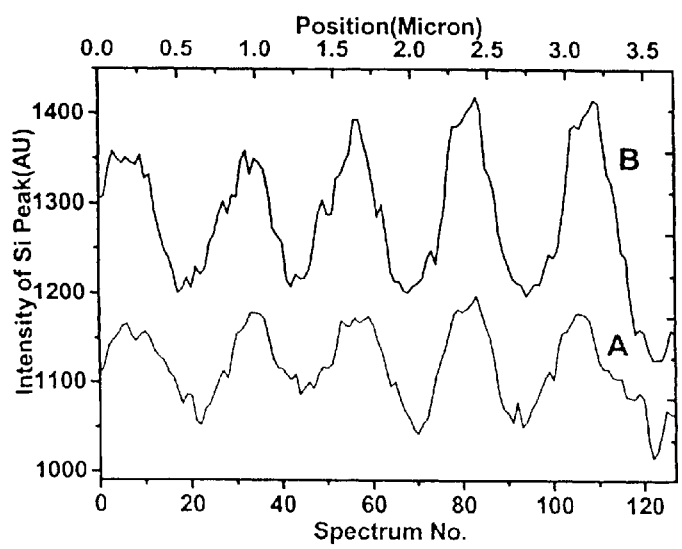
FIG. 6 is a graph showing the Raman intensity mapping of the device sample shown in FIGS. 5A and 5B.

In a second experiment, the system was used to show the improved spatial resolution with the apertureless tip. FIG. 5a shows a cross-section of a silicon device sample while FIG. 5b is an AFM image obtained using the present system. The width of the silicon lines is 300 nm and the SiO$_2$ lines are 380 nm in width, 350 nm in depth and 30 nm higher than the silicon lines. In the experiment, a total of 128 Raman spectra were recorded with one second integration time across the lines. The Raman intensity, peak, width and frequency at each point on the device were derived by fitting the spectra with Gaussian profile using an Array Basic program. In FIG. 6, the Raman intensity of Si is plotted against the serial number of the Raman spectra that corresponds to different positions on the device shown in FIG. 5b (i.e., numbers 1 and 128 are at the left and right most points, respectively). The two curves shown in FIG. 6 are the two Raman mappings of the same Si lines with different tips, showing good reproducibility of the method.

It should be noted that the far-field component of the Si Raman peak comes from the entire illuminated region (3 $\mu$m) which is much larger than the size of the Si or SiO$_2$ lines. Thus, the far-field Raman intensity is independent of the position of the Si device as demonstrated by the featureless micro-Raman mapping. On the other hand, the near-field component comes from a small region (about 100 nm) near the tip only, which shows the variation with the position on the device. Thus, the Raman intensity variation shown in FIG. 6 is a clear manifestation of the near-field enhancement while the far-field Raman contributes a constant background. The stronger intensity was obtained when the tip is on silicon lines, corresponding to valleys in the image and weaker intensity is obtained on $SiO_2$ lines. This can be readily understood that the near-field component is strong when the tip is on silicon, while it is absent when the tip is on the oxide since the oxide is too thick to allow any near-field enhancement of the silicon peak.

A more detailed description of the operation of the device follows in regard to the arrangement of FIG. 1. The metal tip 16 is brought to the sample surface by the cantilever. A red or infrared laser beam emitted from laser diode 20 is focused onto the cantilever and then reflected onto the quadrant detector 22. The position where the reflected laser hits the quadrant detector can be determined according to the output of the detector. During a scan, the distance between the tip and the sample surface is kept constant which is realized by AFM methods, contact mode or tapping mode. In the tapping mode, the cantilever is driven by piezo device 18 in the vibrational amplitude which is a measure of the atomic force between the tip and the sample as detected by the quadrant detector 22. In the contact mode, the quadrant detector detects the bending degree of the cantilever which is also a measure of the atomic force between the tip and the sample.

As mentioned above, the Raman excitation laser beam 24 is much stronger than the laser used for the force sensing. If some of the scattered light from the excitation laser enters the quadrant detector 22, the force detection will be severely effected. To avoid this, a band pass filter is placed just before the quadrant detector to block scattered light. On the other hand, although the laser used for force sensing is weak, compared with the excitation laser, it is still stronger than the reflected Raman signal, so it would have a deleterious effect on the signal to noise ratio of the acquired spectrum if it enters the spectrometer. So a short pass filter or notch filter is placed before the entrance of the spectrometer to avoid this type of problem.

The polarization of the excitation laser has a great effect on the near-field enhancement. A half wave plate is placed into the excitation laser beam. The polarization direction can be rotated by adjusting the half wave plate. To avoid movement of the laser beam while adjusting the plate, the plate should be adjusted perpendicular to the laser beam. In addition to polarization, the incident angle of the excitation laser is another factor effecting the near-field enhancement. When the laser beam is parallel to the tip axis, the enhancement is far from ideal, which can be shown by computer simulation or experiment.

Figure 11A:
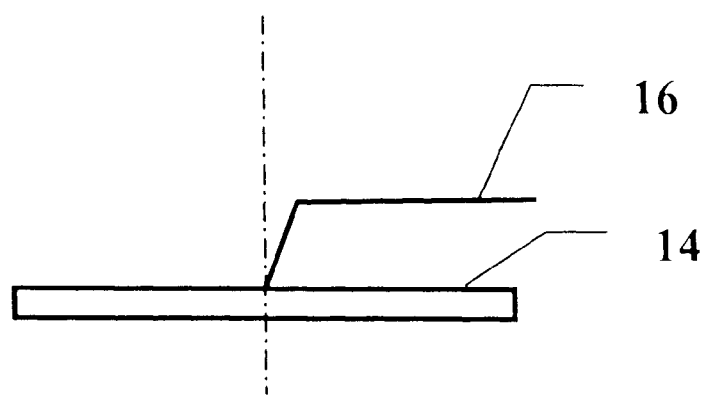
FIGS. 11A and 11B show an arrangement of the tip used in the direction of scanning.
Figure 11B:
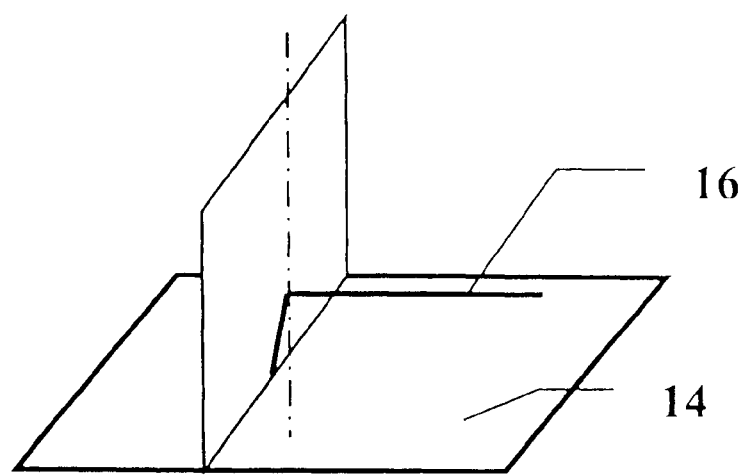

Two approaches can solve this problem. One is to set the tip oblique to the sample surface and use back scattering geometry as shown in FIGS. 11a and 11b. If a left-right scan is used, the oblique configuration in 11a may have a deleterious effect on spatial resolution and may cause the tip to be damaged as well. In this case, the configuration of 11b should be used. When the scan is a back and forth one, based on the same reasoning, the configuration of FIG. 11a should be used.

Another approach is to use a perpendicular tip and oblique incident laser, as shown in FIG. 2. However, rather than using an oblique objective, which requires a specially designed microscope and an objective with a longer working distance, it is possible to use a mirror glued to the tip mount as shown in FIG. 3. This configuration does not require much of an increase in the working distance of the objective so that the existing Nikon objective (NA 0.45 WD 13.8 mm) can still work in this case. There is no difficulty in aligning the laser spot to the tip. In either of the two approaches, the polarization of the excitation laser should be well adjusted to obtain maximum enhancement. Because the incident angle has a great effect on the enhancement, the angle between the tip and the incident laser should be optimized to obtain maximum enhancement. This can be realized by a trial and error method or by a computer simulation.

As to the metal tip, it should be sharp and the cantilever should be flexible and have a high resonance frequency. A flexible cantilever is more sensitive in the force detection. A high resonance frequency can help to suppress noise. Thus, the cantilever should be thin and short. The tip need not be bent, as long as it does not obstruct the light. The metal tip may be metal or metal coated. The tungsten (or other suitable material) tip is prepared using electro-chemical etching, which is similar to but different than STM tip preparation. A suitable tip can be obtained using a tip etching kit (Omicron), a cylindrical stainless steel cathode with a inner diameter of 10 mm, 2-3 M NaOH solution, and a 3.5–4.5 V etching voltage. The etching conditions affect the tip sharpness and length. After being coated with a silver, the tip is bent into a cantilever using an apparatus under a microscope. The silver (or other suitable coating material, with the choice depending on the laser wavelength) coating is obtained through RF-sputtering.

In summary, by using this combination of near-field scanning optical microscopy and Raman spectroscopy, specific information about the chemical structure of materials can be obtained with nano-meter spatial resolution. This is critically important for a wide range of applications including nano-devices, quantum dots, and single molecules biological samples. Using this system a one dimensional Raman mapping and a two dimensional ANSRM image of a real silicon device have been obtained with a one second exposure time. This has been accomplished using back scattering geometry which allows mapping to occur without needing a transparent or very thin sample. It also does not require that the sample be coated with metal or grown on a metal surface. The metal tips used in this apertureless system can be used to make simultaneous AFM and electrical mappings such as resistance and capacitance that are critical parameters for device applications. The system utilizes near-field techniques which has not been possible in the past for signal to noise ratios. Previous systems either used an optical fiber tip with a small (50–200 nm) aperture or resorted to transmission geometries only. The present invention uses an apertureless system in a reflection geometry. The end result is that an image can be constructed in a very short time on the order of one second per point compared to nine hours in some of the prior art. Accordingly, this combination of an NSOM and Raman spectrometer allows the formation of an apertureless near-field Raman microscope using a reflection geometry in order to achieve short processing times and without extensive sample preparation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A Raman spectrographic system, comprising:
   a stage for receiving a sample to be measured;
   a lens for focusing a laser beam to a small spot size on said sample;

an apertureless metal tip at least close to said sample within said laser spot;

said lens collecting Raman scattered light in reflection geometry; and a Raman spectrometer for receiving said collected light and analyzing said sample.

2. The system according to claim 1, wherein said metal tip is coated with metal.

3. The system according to claim 1, wherein said metal tip enhances a near-field Raman signal.

4. The system according to claim 1, wherein the metal tip is cantilevered.

5. The system according to claim 1, further comprising a laser diode and quadrant detector for determining the position of said metal tip.

6. The system according to claim 1, wherein said metal tip is driven by a piezo device.

7. The system according to claim 1, wherein said laser beam is perpendicular to a surface of said sample and said metal tip forms an angle to the sample.

8. The system according to claim 1, wherein said metal tip is vertical to said sample and the focused laser beam forms an angle to said sample.

9. The system according to claim 2, wherein said metal is silver.

10. The system according to claim 1, wherein said lens and said metal tip are on a same side of said stage.

11. A near-field scanning Raman spectrometer, comprising:

a stage for receiving a sample to be measured;

an apertureless metal tip at least close to said sample;

a light beam focused to a small spot by a first lens on the metal tip and said sample;

said metal tip enhancing a near-field Raman signal;

a second lens for collecting Raman shifted light in reflection geometry; and a Raman spectrometer for receiving said collected light and analyzing said sample.

12. The system according to claim 11, wherein said first lens and said second lens are the same lens.

13. The system according to claim 11, wherein said first lens, said second lens and said metal tip are on a same side of said stage.

14. A method of performing apertureless near-field scanning Raman microscopy in reflection geometry, comprising:

focusing a laser beam onto a small spot on a surface of a sample;

placing a metal tip at least close to said surface at a location within said spot;

collecting Raman shifted light in reflection geometry; and applying said collected light to a Raman spectrometer to analyze said sample.

15. The method according to claim 14, further comprising:

enhancing a near-field Raman signal.

16. The method according to claim 14, wherein the laser beam is perpendicular to the surface and the metal tip is cantilevered at an angle to said surface.

17. The method according to claim 14, wherein said focused light is at an angle to a surface of said metal tip is perpendicular to said surface.

18. The method according to claim 14, wherein said metal tip and said laser beam are on a same side of said sample.

* * * * *